US010048210B2

(12) United States Patent
Sato et al.

(10) Patent No.: US 10,048,210 B2
(45) Date of Patent: Aug. 14, 2018

(54) SPECTROSCOPIC ANALYSIS METHOD

(71) Applicant: OLYMPUS CORPORATION, Tokyo (JP)

(72) Inventors: Akira Sato, Tokyo (JP); Shinichi Takimoto, Tokyo (JP)

(73) Assignee: OLYPMUS CORPORATION, Tokyo (JP)

( * ) Notice: Subject to any disclaimer, the term of this patent is extended or adjusted under 35 U.S.C. 154(b) by 0 days.

(21) Appl. No.: 15/233,230

(22) Filed: Aug. 10, 2016

(65) Prior Publication Data

US 2016/0349181 A1    Dec. 1, 2016

Related U.S. Application Data

(63) Continuation of application No. PCT/JP2014/054581, filed on Feb. 25, 2014.

(51) Int. Cl.
*G01N 21/65* (2006.01)
*G01N 21/35* (2014.01)
(Continued)

(52) U.S. Cl.
CPC ............. *G01N 21/65* (2013.01); *G01J 3/28* (2013.01); *G01J 3/42* (2013.01); *G01J 3/44* (2013.01);
(Continued)

(58) Field of Classification Search
CPC . G01N 21/65; G01N 21/35; G01J 3/28; G01J 3/42; G01J 3/44
See application file for complete search history.

(56) References Cited

U.S. PATENT DOCUMENTS

2002/0090145 A1    7/2002  Yamada
2008/0272312 A1    11/2008 Tuschel
(Continued)

FOREIGN PATENT DOCUMENTS

JP    2002-157588 A    5/2002
JP    2010-249835 A1   11/2010
(Continued)

OTHER PUBLICATIONS

International Search Report dated May 27, 2014, issued in PCT/JP2014/054581.
(Continued)

*Primary Examiner* — Hugh H Maupin
(74) *Attorney, Agent, or Firm* — Scully, Scott, Murphy & Presser, P.C.

(57) ABSTRACT

With a spectroscopic analysis method of the present invention, by performing principal component analysis on optical spectra measured at individual positions of a specimen, principal components of a plurality of orders that constitute the individual optical spectra are calculated; for the individual orders, principal-component images in which values thereof are principal-component scores of the individual principal components corresponding to the positions are created; distribution patterns of the principal-component scores are identified in the individual principal-component images; the morphology of the specimen is identified in a morphological image in which the specimen is captured; the principal-component images that have principal-component-score distribution patterns correlated with the morphology of the specimen are identified; and the individual optical spectra are reconstructed by using the principal components of orders corresponding to the orders of the identified principal-component images.

3 Claims, 4 Drawing Sheets

(51) Int. Cl.
*G01J 3/28* (2006.01)
*G01J 3/42* (2006.01)
*G01J 3/44* (2006.01)

(52) U.S. Cl.
CPC ..... *G01N 21/35* (2013.01); *G01N 2201/1293* (2013.01)

(56) References Cited

U.S. PATENT DOCUMENTS

| | | |
|---|---|---|
| 2011/0248166 A1 | 10/2011 | Diem et al. |
| 2012/0046555 A1 | 2/2012 | Takamatsu et al. |
| 2012/0082362 A1 | 4/2012 | Diem et al. |
| 2012/0083678 A1* | 4/2012 | Drauch ............... A61B 5/0075 600/310 |
| 2012/0328178 A1 | 12/2012 | Remiszewski et al. |
| 2015/0142333 A1 | 5/2015 | Diem et al. |
| 2016/0012591 A1 | 1/2016 | Remiszewski et al. |

FOREIGN PATENT DOCUMENTS

| | | |
|---|---|---|
| JP | 2013-524246 A | 6/2013 |
| JP | 2013-535014 A | 9/2013 |
| JP | 2014-38044 A | 2/2014 |
| WO | 2010/103661 A1 | 9/2010 |
| WO | 2011/127474 A1 | 10/2011 |
| WO | 2011/163624 A1 | 12/2011 |
| WO | 2013/146779 A1 | 10/2013 |

OTHER PUBLICATIONS

Hutchings, J., et al., "The potential for histological screening using a combination of rapid Raman mapping and principal component analysis", Journal of Biophotonics, Jan. 28, 2009, pp. 91-103, vol. 2, No. 1-2.

Sasic, S., et al., "A comparison of Raman chemical images produced by univariate and multivariate data processing—a simulation with an example from pharmaceutical practice" Analyst, Oct. 7, 2004, pp. 1001-1007, vol. 129.

* cited by examiner

SPECTROSCOPIC ANALYSIS METHOD

CROSS-REFERENCE TO RELATED APPLICATIONS

This is a continuation of International Application PCT/JP2014/054581 which is hereby incorporated by reference herein in its entirety.

TECHNICAL FIELD

The present invention relates to a spectroscopic analysis method.

BACKGROUND ART

In the related art, spectral measurement methods have been employed as methods for analyzing components of specimens such as tissue slices (for example, see Non-Patent Literatures 1 and 2). Raman scattered light coming from individual positions of a specimen is detected, Raman spectra are acquired by diffracting the detected Raman scattered light, and scalar values related to components at the individual positions of the specimen are obtained by performing principal component analysis on a collection of the acquired Raman spectra.

The acquired Raman spectra include components derived from various types of noise, such as scattered light coming from the slide glass on which the specimen is placed, autofluorescence of an optical element, thermal noise of a detector, and so forth. Principal component analysis has also effectively been utilized in processing for removing these noise-derived components from the acquired Raman spectra. Specifically, higher-order principal components are removed, assuming that the higher-order principal components obtained by means of principal component analysis are components derived from noise, and Raman spectra are reconstructed by using only lower-order principal components.

CITATION LIST

Non-Patent Literature

{NPL 1} Slobodan Sasic and two others, "A comparison of Raman chemical images produced by univariate and multivariate data processing—a simulation with an example from pharmaceutical practice", Analyst, 129, pp. 1001-1007, 2004

{NPL 2} Joanne Hutchings and five others, "The potential for histological screening using a combination of rapid Raman mapping and principal component analysis", Journal of Biophotonics, vol. 2, no. 1-2, pp. 91-103, 2009

SUMMARY OF INVENTION

Solution to Problem

The present invention provides a spectroscopic analysis method including: a principal-component analyzing step of calculating, by performing principal component analysis on a collection of optical spectra measured at individual positions of a specimen, principal components of a plurality of orders that constitute the individual optical spectra; a principal-component-image creating step of creating, for the individual orders, principal-component images in which values thereof are principal-component scores of the individual principal components obtained in the principal-component analyzing step, corresponding to the positions; a first identifying step of identifying distribution patterns of the principal-component scores in the individual principal-component images created in the principal-component-image creating step; a second identifying step of identifying the morphology of the specimen in a morphological image in which the specimen is captured; a comparing step of comparing the distribution patterns of the principal-component scores identified in the first identifying step with the morphology of the specimen identified in the second identifying step and of identifying principal-component images that have the distribution patterns correlated with the morphology of the specimen; and a reconstructing step of reconstructing the individual optical spectra by using, among the principal components obtained in the principal-component analyzing step, principal components in which orders thereof correspond to orders of the principal-component images identified in the comparing step.

DESCRIPTION OF EMBODIMENT

A spectroscopic analysis method according to an embodiment of the present invention will be described below with reference to the drawings.

Figure 1:
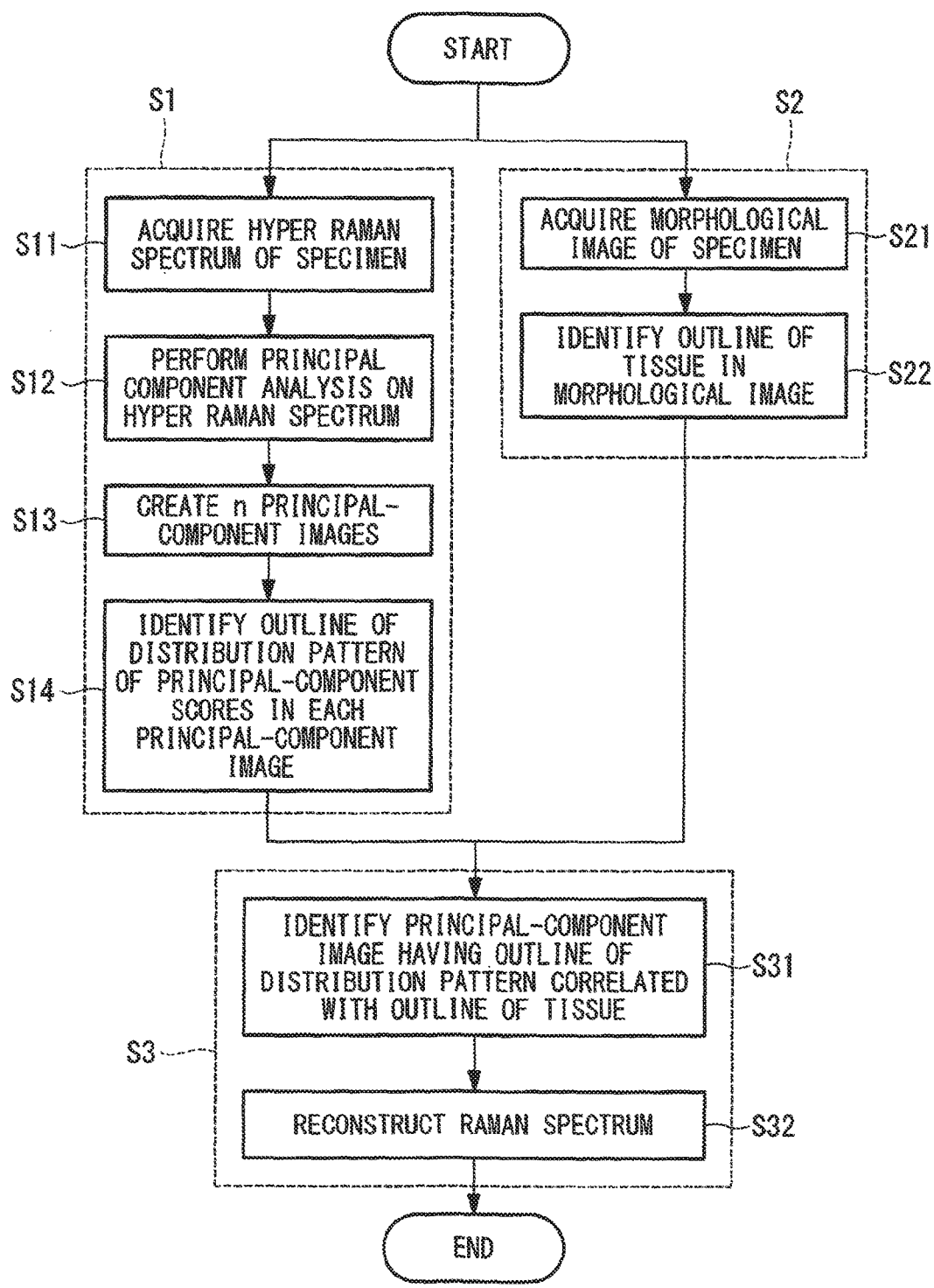
FIG. 1 is a flowchart showing a spectroscopic analysis method according to an embodiment of the present invention.

As shown in FIG. 1, the spectroscopic analysis method according to this embodiment includes, in a rough classification: a first step S1 of creating, by means of principal component analysis, principal-component images from a collection of Raman spectra (hyper Raman spectrum) measured at individual positions of a specimen A and of processing the principal-component images; a second step S2 of processing a morphological image of the specimen; and a third step S3 of obtaining Raman spectra from which noise has been removed by using the principal-component images and the morphological image.

Such a spectroscopic analysis method is employed in a microscope system that is provided with a microscope with which it is possible to acquire the optical spectra and the morphological image of the specimen and a control device that analyzes the optical spectra and the morphological image acquired by the microscope. For example, the control device is a computer provided with a CPU (Central Processing Unit) and a storage device, and a program for executing the first step S1 to the third step S3 is stored in the storage device. Then, the CPU reads out the program from the storage device and executes the program, thus performing the processing from the first step S1 to the third step S3, described above. Alternatively, the control device may be provided with a first processing portion, a second processing portion, and a third processing portion as special hardware for individually executing the processing for the first step S1, the second step S2, and the third step S3.

Note that, in this embodiment, although Raman spectra will be described as the optical spectra, other types of optical spectra, for example, infrared absorption spectra or the like, can be suitably used in the spectroscopic analysis method according to this embodiment.

The first step S1 includes: a spectra-acquiring step S11 of acquiring a hyper spectrum by measuring Raman spectra at individual positions of the specimen by using the microscope; a principal-component analyzing step S12 of performing principal component analysis on the hyper spectrum acquired in the spectra-acquiring step S11; a principal-component-image creating step S13 of creating n principal-component images by using the results of the principal component analysis; and a score-pattern identifying step (first identifying step) S14 of identifying distribution patterns of the individual principal-component scores from the individual principal-component images created in the principal-component-image creating step S13.

Figure 2:
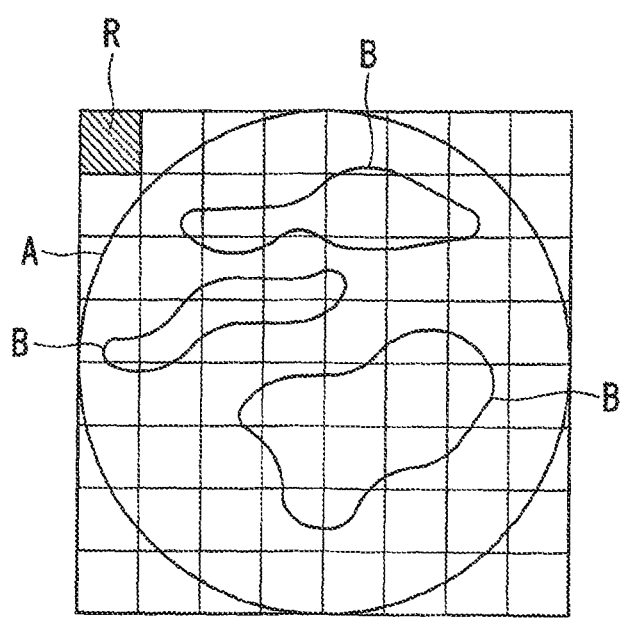
FIG. 2 is a diagram for explaining the relationship between a specimen, which is the measurement target of the spectroscopic analysis method of FIG. 1, and sections in which Raman spectra are measured in a spectra-acquiring step.

The specimen is, for example, a tissue slice attached to the surface of a slide glass. As shown in FIG. 2, in the spectra-acquiring step S11, the surface of the specimen A is divided into a plurality of sections R, Raman scattering from the sections R is detected by using a CCD detector by sequentially radiating laser light onto the individual sections R, and Raman spectra of the individual sections are acquired by diffracting the detected Raman spectra. Then, a hyper Raman spectrum is acquired by collecting the Raman spectra of all of the sections R.

In the principal-component analyzing step S12, principal components of the first order to the $n^{th}$ order are calculated by performing principal component analysis on the hyper Raman spectrum acquired in the spectra-acquiring step S11. By using a first principal component axis V1, a second principal component axis V2, a third principal component axis V3, . . . , and an $n^{th}$ principal component axis Vn obtained by means of the principal component analysis, Raman spectra of the individual sections R are expressed by the following expression.

$$V = C1 \times V1 + C2 \times V2 + C3 \times V3 + \ldots + Cn \times Vn$$

Here, the Raman spectra V are expressed as vectors. In addition, Ci (i=1, 2, 3, . . . , n) are $i^{th}$ principal-component scores expressed as inner products of the $i^{th}$ principal component axes Vi and the Raman spectra V of the individual sections R, and they serve as scalar values.

Figure 3:
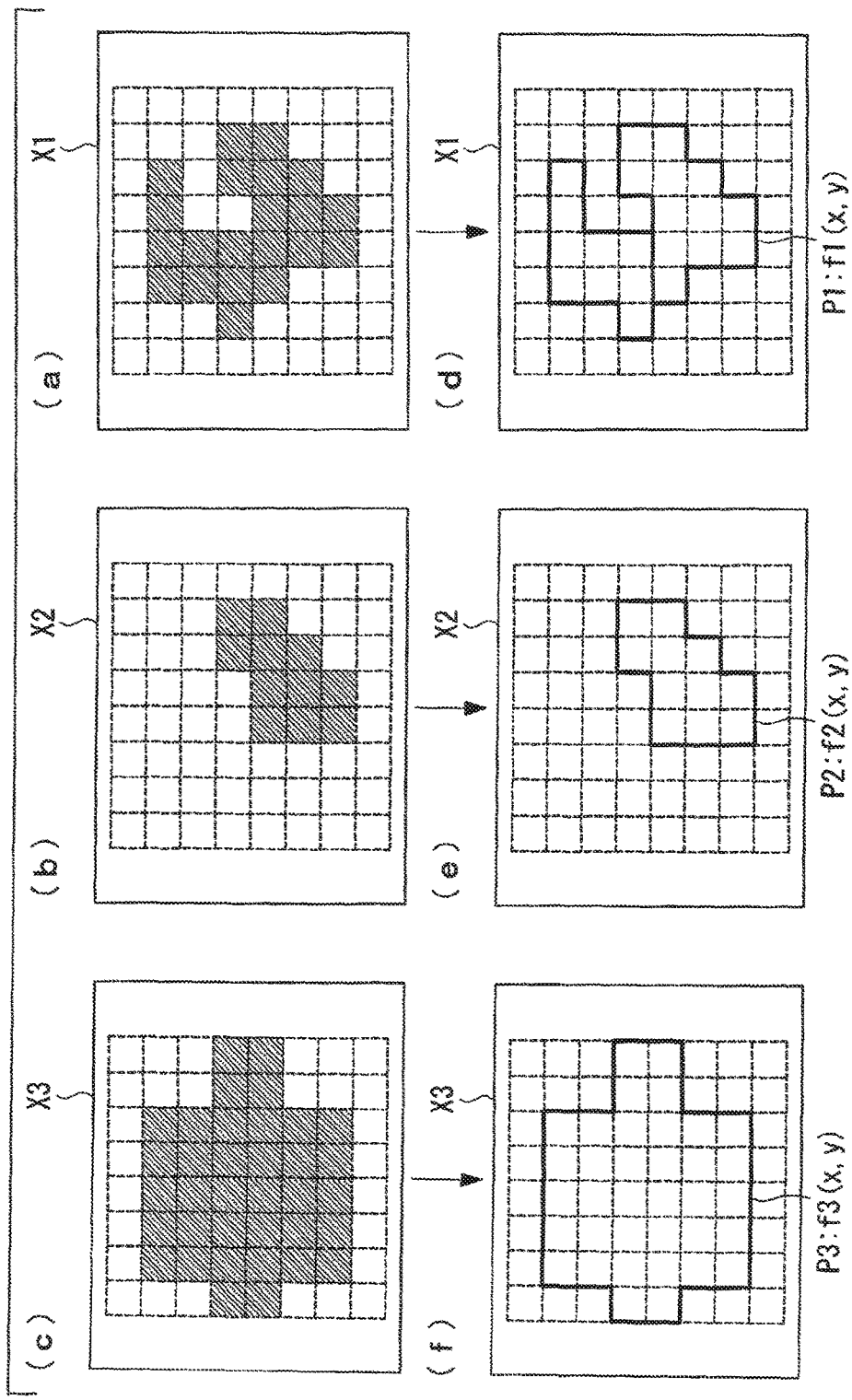
FIG. 3 is a diagram showing, in (a), (b), and (c), first, second, and third principal-component images, and, in (d), (e), and (f), outlines of distribution patterns of principal-component scores identified in the individual principal-component images.

In the score-pattern identifying step S14, outlines Pi of score distribution patterns are identified from the $i^{th}$ principal-component images Xi created in the principal-component-image creating step S13. To identify the outlines Pi of the distribution patterns, for example, edge detection processing is employed. Specifically, functions that express changes of the scores in the $i^{th}$ principal-component images Xi are calculated, differential coefficients at individual positions of the calculated functions are calculated, and positions at which the calculated differential coefficients are greater than a predetermined threshold are identified as the outlines Pi. FIGS. 3(d), (e), and (f) individually show outlines P1, P2, and P3 of the score distribution patterns identified in a first principal-component image X1, a second principal-component image X2, and a third principal-component image X3.

The second step S2 includes: a morphological-image acquiring step S21 of acquiring the morphological image of the specimen A; and a morphology identifying step (second identifying step) S22 of identifying the morphology of the specimen A in the morphological image.

Figure 4:
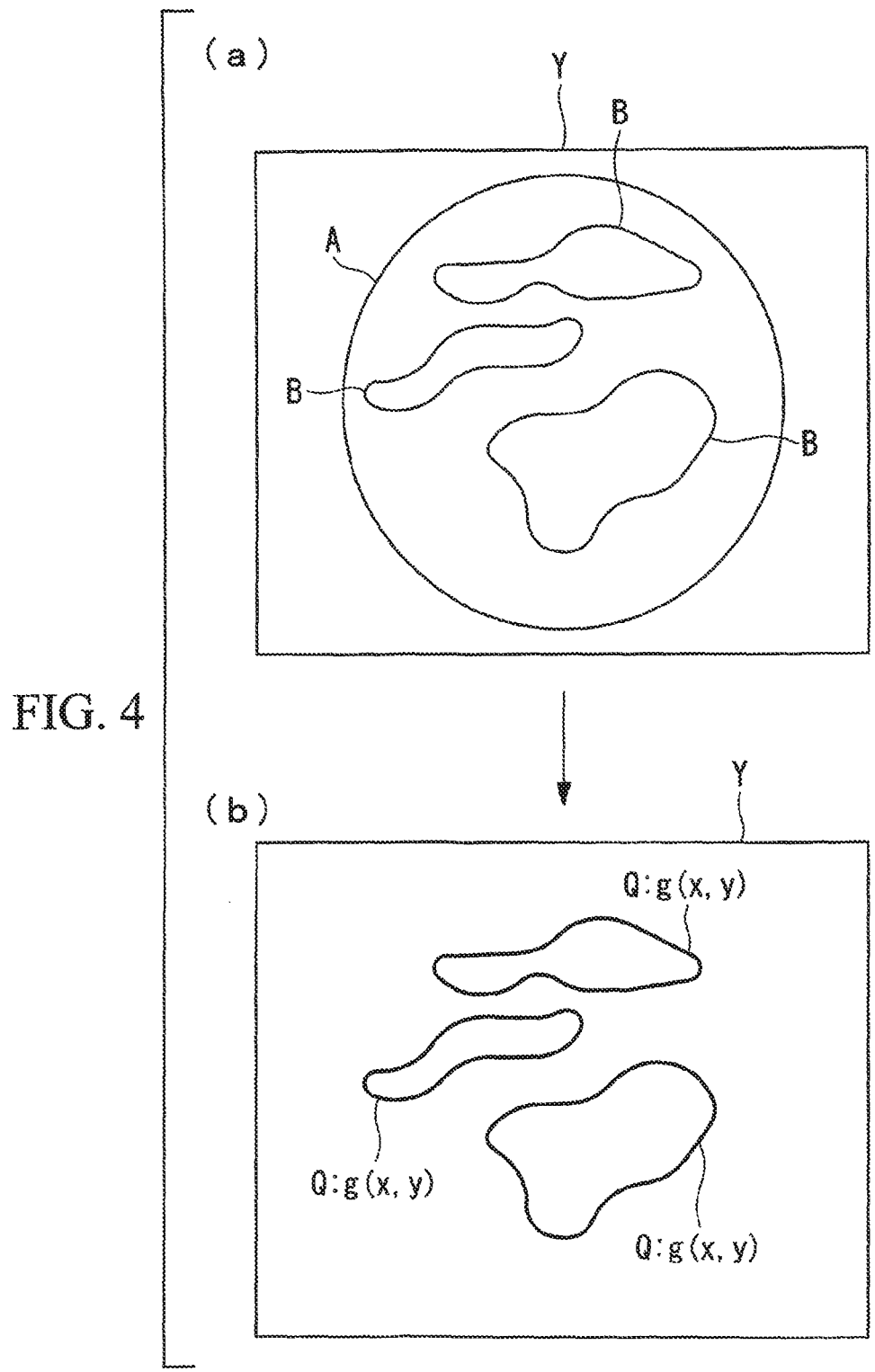
FIG. 4 is a diagram showing: (a) a morphological image; and (b) outlines of tissue identified in the morphological image.

As shown in FIG. 4(a), in the morphological-image acquiring step S21, a morphological image Y in which the specimen A is captured is acquired by using the optical microscope. A phase-contrast image, a differential-interference-contrast image, or a bright-field image in which tissue B contained the specimen A is clearly captured is preferable as the morphological image Y.

In the morphology identifying step S2, as shown in FIG. 4(b), outlines Q of the tissue B (for example, blood vessels, fibrous tissue, or the like) contained in the specimen A are identified in the morphological image Y acquired in the morphological-image acquiring step S21. To identify the outlines Q of the tissue B, for example, edge detection processing is employed, as with the above-described score-pattern identifying step S14. Specifically, functions expressing changes in luminance in the morphological image Y are calculated, differential coefficients of the individual positions of the calculated functions are calculated, and positions at which the calculated differential coefficients are greater than a predetermined threshold are identified as the outlines Q.

The third step S3 includes: a comparing step S31 of comparing the outlines Pi identified in the $i^{th}$ principal-component images Xi and the outlines Q identified in the morphological image Y and of searching for outlines Pi that correlate with the outlines Q; and a reconstructing step S32 of reconstructing Raman spectra of the individual sections on the basis of the order i of the $i^{th}$ principal-component images Xi that have the outlines Pi judged to be qualified in the comparing step S31.

In the comparing step S31, the outlines Pi of the score distribution patterns are compared with the outlines Q of the tissue B, thus searching for outlines Pi in which the shape thereof are similar to that of the outlines of the tissue B. For example, functions fi(x, y) that express the shape of the outlines Pi of the distribution patterns of the individual scores and functions g(x, y) that express the shape of the outlines Q of the tissue B are calculated, the differences between the two sets of functions f(x, y) and gi(x, y) at individual positions (x, y) are squared, and the calculated squared values are integrated across all positions (x, y) Note that, in FIGS. 3(f) to (d), the lateral direction in the individual images X1, X2, and X3 is the x-axis, and the vertical direction therein is the y-axis.

The calculated integrals reflect the magnitude of correlation between the two sets of functions f(x, y) and gi(x, y). In the case in which the integrals are equal to or less than a predetermined threshold, the two sets of outlines Pi and Q are assumed to be sufficiently similar, and thus, the $i^{th}$ principal-component image Xi corresponding to these Pi are selected. By doing so, among the n principal-component images X1 to Xn, the $i^{th}$ principal-component images Xi in which the score distribution patterns thereof have a sufficiently high correlation with respect to the morphology of the specimen A in the morphological image Y are identified.

In the reconstructing step S32, the Raman spectra of the individual pixels are reconstructed by using the $i^{th}$ principal components that constitute the $i^{th}$ principal-component images Xi identified in the comparing step S31. Specifically, as has been described above, measured raw Raman spectra V are constituted of n principal components $C1 \times V1$, $C2 \times V2$, $C3 \times V3$, $Cn \times Vn$. Among these n principal components $C1 \times V1$, $C2 \times V2$, $C3 \times V3$, $Cn \times Vn$, principal components that correspond to the principal-component images that were not selected in the comparing step S31 are removed. For example, in the case in which the first principal-component image, the second principal-component image, the third principal-component image, and the seventh principal-component image are identified in the comparing step S31, a reconstructed Raman spectrum V' of each section R would be:

$$V'=C1\times V1+C2\times V2+C3\times V3+C7\times V7.$$

As has been described above, with this embodiment, by comparing the morphological image Y with the n principal-component images X1, X2, X3, . . . , Xn obtained by performing the principal component analysis on the hyper Raman spectrum, the principal components that have sufficiently high correlation with respect to the morphology of the specimen A are identified. The principal components that were not identified are the principal components that have no correlation or sufficiently low correlation with respect to the morphology of the specimen A, and thus, they are principal components derived from noise such as the thermal noise of a CCD detector, scattered light coming from a slide glass, or the like. By removing such nose-derived principal components from the n principal components $C1\times V1$, $C2\times V2$, $C3\times V3$, . . . , $Cn\times Vn$ that constitute the raw Raman spectra V, it is possible to obtain accurate Raman spectra V' of the Raman scattered light emitted from the specimen A.

In addition, Raman scattered light that is equivalent to or even weaker than low noise such as thermal noise is included in higher-order principal components having low eigenvalues. On the other hand, large noise such as scattered light coming from a slide glass or an optical element provided in a microscope is included in lower-order principal components having large eigenvalues. With this embodiment, regardless of the order thereof, the principal components derived from Raman scattered light coming from the specimen A are distinguished from the principal components derived from noise on the basis of the degree of correlation with respect to the morphology of the specimen A, the principal components that have sufficiently high correlation with respect to the morphology of the specimen A are left in the reconstructed Raman spectra V', and the principal components that have sufficiently low correlation with respect to the morphology of the specimen A are removed. Specifically, information about weak Raman scattered light that appears in higher-order principal components is not lost together with noise, and, in addition, large noise that appears in lower-order principal components is reliably removed. Accordingly, there is an advantage in that it is possible to appropriately remove various types of noise by performing processing just once.

The above-described embodiment leads to the following inventions.

The present invention provides a spectroscopic analysis method including: a principal-component analyzing step of calculating, by performing principal component analysis on a collection of optical spectra measured at individual positions of a specimen, principal components of a plurality of orders that constitute the individual optical spectra; a principal-component-image creating step of creating, for the individual orders, principal-component images in which values thereof are principal-component scores of the individual principal components obtained in the principal-component analyzing step, corresponding to the positions; a first identifying step of identifying distribution patterns of the principal-component scores in the individual principal-component images created in the principal-component-image creating step; a second identifying step of identifying the morphology of the specimen in a morphological image in which the specimen is captured; a comparing step of comparing the distribution patterns of the principal-component scores identified in the first identifying step with the morphology of the specimen identified in the second identifying step and of identifying principal-component images that have the distribution patterns correlated with the morphology of the specimen; and a reconstructing step of reconstructing the individual optical spectra by using, among the principal components obtained in the principal-component analyzing step, principal components in which orders thereof correspond to orders of the principal-component images identified in the comparing step.

With the present invention, by performing principal component analysis on the hyper Raman spectrum, which is a collection of the optical spectra of the specimen, in the principal-component analyzing step, the plurality of principal components constituting the optical spectra of individual positions of the specimen are separated, and the principal-component images are created in the principal-component-image creating step by using the separated principal components. Then, in the first identifying step, distribution patterns of the principal-component scores are identified in the individual principal-component images, whereas, in the second identifying step, the morphology of the specimen is identified from the morphological image of the specimen.

Next, in the comparing step, the principal-component images having the distribution patterns of the principal-component scores that correlate with the morphology of the specimen are identified among the plurality of principal-component images. Specifically, among the plurality of principal components that have been separated in the principal-component analyzing step, the principal components derived from the morphology of the specimen are distinguished from the principal components derived from noise. In the reconstructing step, among the plurality of principal components, optical spectra that contain only the principal components that have been judged to be derived from the morphology of the specimen in the comparing step are reconstructed. By doing so, it is possible to obtain accurate optical spectra by appropriately removing various types of noise all at once.

In the above-described invention, the optical spectra may be Raman spectra or infrared absorption spectra.

By doing so, it is possible to perform analysis for specific molecules contained in the specimen.

In the above-described invention, the morphological image may be a phase-contrast image, a differential-interference-contrast image, or a bright-field image.

By doing so, by using a phase-contrast image, a differential-interference-contrast image, or a bright-field image in which the morphology of the specimen is clearly captured, it is possible to more accurately identify the morphology of the specimen in the second identifying step.

REFERENCE SIGNS LIST

S11 spectra-acquiring step
S12 principal-component analyzing step
S13 principal-component-image creating step
S14 score-pattern identifying step (first identifying step)
S21 morphological-image acquiring step
S22 morphology identifying step (second identifying step)
S31 comparing step
S32 reconstructing step
A specimen
B tissue R section
X1, X2, X3 principal-component image
Y morphological image
P1, P2, P3 outline
Q outline

The invention claimed is:

1. A spectroscopic analysis method comprising:

a principal-component analyzing step of calculating, by performing principal component analysis on a collection of optical spectra measured at individual positions of a specimen, principal components of a plurality of orders that constitute the individual optical spectra;

a principal-component-image creating step of creating, for the individual orders, principal-component images in which values thereof are principal-component scores of the individual principal components obtained in the principal-component analyzing step, corresponding to the positions;

a first identifying step of identifying outlines of distribution patterns of the principal-component scores in the individual principal-component images created in the principal-component-image creating step;

a second identifying step of identifying an outline of morphology of the specimen in a morphological image in which the specimen is captured;

a comparing step of comparing the outlines of distribution patterns of the principal-component scores identified in the first identifying step with the outline of the morphology of the specimen identified in the second identifying step and of identifying one or more of the principal-component images that have the outlines of distribution patterns correlated with the outline of morphology of the specimen; and a reconstructing step of reconstructing the individual optical spectra by: adding one or more of the principal components in which orders thereof correspond to orders of the one or more of the principal-component images identified in the comparing step and correlated with the outline of morphology of the specimen; and removing, from the individual optical spectra, rest of the principal components other than the one or more of the principal components.

2. A spectroscopic analysis method according to claim 1, wherein the optical spectra are Raman spectra or infrared absorption spectra.

3. A spectroscopic analysis method according to claim 1, wherein the morphological image is a phase-contrast image, a differential-interference-contrast image, or a bright-field image.

* * * * *